(12) United States Patent
Machado et al.

(10) Patent No.: US 12,194,297 B2
(45) Date of Patent: Jan. 14, 2025

(54) CONFIGURING A DEEP BRAIN STIMULATION (DBS) SYSTEM TO TREAT A NEUROLOGICAL DISORDER

(71) Applicant: THE CLEVELAND CLINIC FOUNDATION, Cleveland, OH (US)

(72) Inventors: Andre Machado, Pepper Pike, OH (US); Raghavan Gopalakrishnan, Brecksville, OH (US); Kenneth Baker, Chesterland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 17/154,045

(22) Filed: Jan. 21, 2021

(65) Prior Publication Data

US 2021/0228880 A1    Jul. 29, 2021

Related U.S. Application Data

(60) Provisional application No. 62/964,710, filed on Jan. 23, 2020.

(51) Int. Cl.
*A61N 1/36* (2006.01)
*A61N 1/05* (2006.01)

(52) U.S. Cl.
CPC ....... *A61N 1/36067* (2013.01); *A61N 1/0534* (2013.01); *A61N 1/36135* (2013.01)

(58) Field of Classification Search
CPC .............. A61N 1/36067; A61N 1/0534; A61N 1/36135; A61N 1/36139
See application file for complete search history.

(56) References Cited

U.S. PATENT DOCUMENTS 7,640,063 B2    12/2009 Rezai et al.
8,190,263 B2    5/2012 Machado et al.
(Continued)

FOREIGN PATENT DOCUMENTS

WO    2017/010930 A1    1/2017
WO    2018/213872 A1    11/2018
WO    2019027512 A1    2/2019

OTHER PUBLICATIONS

Wagle Shukla A, Zeilman P, Fernandez H, Bajwa JA, Mehanna R. DBS Programming: An Evolving Approach for Patients with Parkinson's Disease. Parkinsons Dis. 2017;2017:8492619. doi: 10.1155/2017/8492619. Epub Sep. 24, 2017. PMID: 29147598; PMCID: PMC5632902. (Year: 2017).*

(Continued)

*Primary Examiner* — Joseph M Dietrich
(74) *Attorney, Agent, or Firm* — Tarolli, Sundheim, Covell & Tummino LLP

(57) ABSTRACT

Deep brain stimulation (DBS) can be used to treat many neurological conditions beyond traditional movement disorders. When patients do not suffer from traditional movement disorders, medical professionals cannot use traditional observation-based methods to configure the DBS system. A new method for selecting stimulation configurations can include recording internal data and external data as the patient performs (or attempts to perform) a motor task. The internal data is electrophysiology data recorded by a plurality of DBS electrodes, used to identify at least one of the plurality of electrodes closest to a neuronal population involved in control of the at least one motor task. The external data is electroencephalogram (EEG) data recorded by scalp electrodes, which is used to select at least one of the potential stimulation electrodes to deliver the DBS. When (Continued)

the electrode(s) delivering the DBS are selected, optimal parameters for the DBS are then chosen.

20 Claims, 18 Drawing Sheets

(56) References Cited

U.S. PATENT DOCUMENTS

| | | | |
|---|---|---|---|
| 9,289,603 | B1 | 3/2016 | Giuffrida et al. |
| 2009/0234419 | A1* | 9/2009 | Maschino .............. A61N 2/006 607/45 |
| 2012/0150262 | A1* | 6/2012 | Gliner ................ A61N 1/36071 607/62 |
| 2013/0184781 | A1* | 7/2013 | Eskandar ........... A61N 1/36167 607/45 |
| 2015/0105837 | A1* | 4/2015 | Aguilar Domingo . A61B 5/374 607/45 |
| 2016/0022168 | A1* | 1/2016 | Luczak ................. A61B 5/377 607/45 |
| 2016/0082263 | A1* | 3/2016 | Jaseja ................ A61N 1/36139 607/45 |
| 2016/0220821 | A1 | 8/2016 | O'Connell et al. |
| 2017/0113048 | A1* | 4/2017 | Giftakis ............. A61N 1/36082 |
| 2018/0085586 | A1 | 3/2018 | Stanslaski et al. |
| 2018/0104500 | A1* | 4/2018 | Blum ................ A61N 1/36139 |
| 2018/0193649 | A1* | 7/2018 | Schouenborg ..... A61N 1/36085 |
| 2018/0326217 | A1 | 11/2018 | Giftakis et al. |
| 2020/0086127 | A1* | 3/2020 | Intrator .............. A61N 1/36139 |
| 2020/0138324 | A1* | 5/2020 | Sinclair .............. A61N 1/36139 |

OTHER PUBLICATIONS

Wathen, C. A., Frizon, L. A., Maiti, T. K., Baker, K. B., & Machado, A. G. (2018). Deep brain stimulation of the cerebellum for poststroke motor rehabilitation: from laboratory to clinical trial. Neurosurgical focus, 45(2), E13 (Year: 2018).*

PCT International Search Report and Written Opinion for corresponding International Application Serial No. PCT/US2021/014283, mailed Apr. 19, 2021, pp. 1-16.

Wathen, Connor A., et al. "Deep brain stimulation of the cerebellum for poststroke motor rehabilitation: from laboratory to clinical trial." Neurosurgical focus 45.2 (2018): E13.

Wagner, Tim, et al. "Transcranial magnetic stimulation and stroke: a computer-based human model study." Neuroimage 30.3 (2006): 857-870.

Cooper, Irving S., A. R. Upton, and I. Amin. "Chronic cerebellar stimulation (CCS) and deep brain stimulation (DBS) in involuntary movement disorders." Applied neurophysiology 45.3 (1982): 209-217.

Wu, Jennifer, et al. "Connectivity measures are robust biomarkers of cortical function and plasticity after stroke." Brain 138.8 (2015): 2359-2369.

Canadian Office Action for Corresponding Application Serial No. PCT No. US 2021014283, Dated Jun. 2, 2023, pp. 1-5.

IP Australia Examination Report No. 1, dated Feb. 15, 2024 for corresponding application No. 2023201540, Applicant name: The Cleveland Clinic Foundation, pp. 1-3.

Australian Examination Report for Corresponding Application Serial No. 2021210896, Dated Oct. 5, 2022, pp. 1-4.

European Patent Office Examination Report for Application No. 21 705 763.7-1126, Applicant The Cleveland Clinic Foundation, dated Jan. 22, 2024; 4 pages.

* cited by examiner

```
                  ┌──────────────────────────────────┐
                  │ 52                               │
             50 ↘ │   ELECTRODE CAUSES SIDE EFFECTS? │
                  └──────────────────────────────────┘
                                   │
                                   ▼
                  ┌──────────────────────────────────┐
                  │ 54                               │
                  │         LOCAL EFFECTS?           │
                  └──────────────────────────────────┘
                                   │
                                   ▼
                  ┌──────────────────────────────────┐
                  │ 56                               │
                  │         ACUTE EFFECTS?           │
                  └──────────────────────────────────┘
                                   │
                                   ▼
                  ┌──────────────────────────────────┐
                  │ 58                               │
                  │             TITRATE              │
                  └──────────────────────────────────┘
```

FIG. 5

CONFIGURING A DEEP BRAIN STIMULATION (DBS) SYSTEM TO TREAT A NEUROLOGICAL DISORDER

RELATED APPLICATIONS

This application claims priority to U.S. Provisional Application Ser. No. 62/964,710, filed Jan. 23, 2020, entitled "Biomarkers for DBS Programming and Control". The entirety of this provisional application is hereby incorporated by reference for all purposes.

GOVERNMENT SUPPORT

This invention was made with government support under NS100543 awarded by the National Institutes of Health. The government has certain rights in this invention.

TECHNICAL FIELD

The present disclosure relates generally to deep brain stimulation (DBS) and, more specifically, to systems and methods for configuring a DBS system to stimulate a cerebellar pathway connecting to a brainstem, a diencephalon, or a cerebrum of a patient to treat a neurological disorder in the patient.

BACKGROUND

For years, deep brain stimulation (DBS) has been used to control spurious brain activity causing unwanted movements connected to movement disorders, such as Parkinson's disease and essential tremor. DBS electrodes have been implanted in a patient's brain in one or more areas known to experience the spurious brain activity and one or more of these DBS electrodes can be used to deliver electrical stimulation to the one or more areas. The electrical stimulation can be specifically configured to modulate the spurious brain activity, thereby reducing the unwanted movements (e.g., tremor, rigidity, and the like).

A medical professional can observe when the unwanted movement stops, so configuration of the DBS system and the electrical stimulation is straightforward. The medical professional tests a series of settings and observes the corresponding improvement or worsening of symptoms of the unwanted movement. These settings can be programmed into the DBS system, leading to good management of the unwanted movement over a long term. When DBS is used for purposes other than stopping unwanted movement, however, the stimulation settings cannot be chosen based on observation alone. When DBS is used to stimulate a cerebellar pathway connecting to a brainstem, a diencephalon, or a cerebrum to treat different neurological conditions, different methods must be used to find the stimulation configurations.

SUMMARY

The present disclosure relates to systems and methods for configuring a deep brain stimulation (DBS) system to stimulate a cerebellar pathway connecting to a brainstem, a diencephalon, or a cerebrum of a patient to treat a neurological disorder in the patient.

In an aspect, the present disclosure can include a system that configures the DBS system. The system can include a memory storing instructions and a processor to access the memory and execute the instructions to: receive electrophysiology data from a plurality of implanted DBS electrodes (e.g., implanted in at least one cerebellar pathway connecting to a brainstem, a diencephalon, or a cerebrum of the patient) and electroencephalogram (EEG) data corresponding to at least one scalp EEG from a plurality of scalp electrodes in response to the patient performing or attempting to perform at least one motor task; based on the electrophysiology data, identify at least one of the plurality of electrodes implanted closest to a neuronal population involved in control of the at least one motor task as potential stimulation electrodes and based on the EEG data and/or electrophysiological data from the DBS electrodes, select at least one of the potential stimulation electrodes to deliver the DBS based on which of the potential stimulation electrodes provides a change in the EEG data and/or in the data from the DBS electrodes; and determining optimal parameters for the DBS. The optimal parameters for the DBS and the at least one of the potential stimulation electrode to deliver the DBS are output for guiding configuration of the DBS system for the patient.

In another aspect, the present disclosure can include a method for configuring the DBS system. The method can include instructing the patient to perform or attempt to perform at least one motor task. In response to the patient performing or attempting to perform the at least one motor task, a system that includes a processor can execute steps of the method, including: receiving electrophysiology data from a plurality of DBS electrodes implanted in at least one cerebellar pathway connecting to a brainstem, a diencephalon, or a cerebrum of the patient; based on the electrophysiology data, identifying, by the system, at least one of the plurality of electrodes implanted closest to a neuronal populations involved in control of the at least one motor task as potential stimulation electrodes; in response to the patient performing or attempting to perform the at least one motor task, receiving EEG data corresponding to at least one scalp EEG from a plurality of scalp electrodes and/or data from at least one DBS electrode; based on the EEG data and/or DBS electrode data, selecting at least one of the potential stimulation electrodes to deliver the DBS based on which of the potential stimulation electrodes provides a change in the EEG data and/or DBS electrode data; and determining optimal parameters for the DBS by the at least one of the potential stimulation electrodes. The optimal parameters for the DBS and the at least one of the potential stimulation electrode to deliver the DBS are output for guiding configuration of the DBS system for the patient.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 5 is a process flow diagram illustrating a method showing the approach for configuring the DBS system used experimentally;

DETAILED DESCRIPTION

I. Definitions

Figure 1:
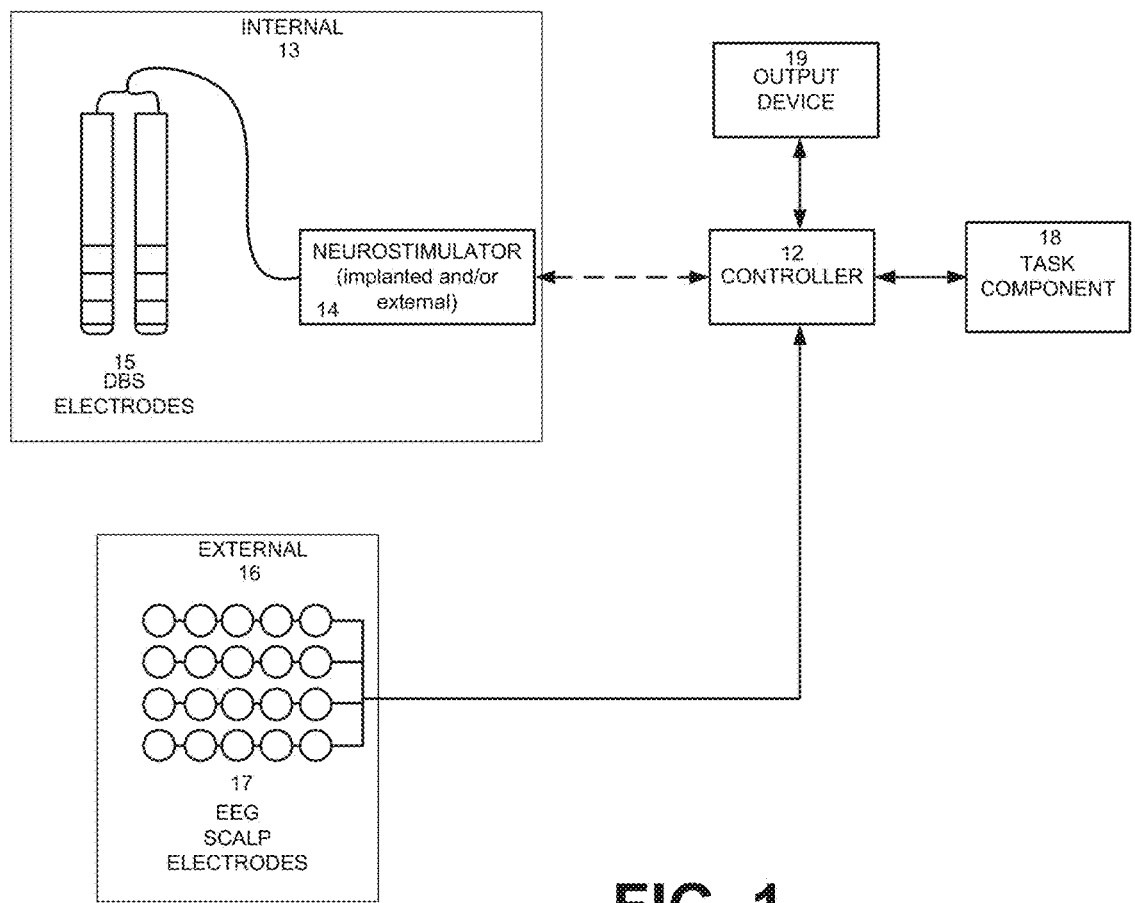
FIG. 1 is a diagram showing an example of a system that can be used to configure a DBS system to stimulate a cerebellar pathway connecting to a brainstem, a diencephalon, or a cerebrum of a patient to treat a neurological disorder in the patient in accordance with an aspect of the present disclosure.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "deep brain stimulation", represented by the abbreviation DBS, refers to electrical stimulation applied to target sites within specific regions of the brain by electrodes implanted within the specific regions. In some instances, the electrical stimulation can be chronically applied.

As used herein, the terms "neurological disorder" and "neurological condition" refer to a structural, biochemical, and/or electrical abnormality in the brain, spinal cord, or peripheral nerves. The neurological condition treated with DBS can be an electrical abnormality within the brain. For example, DBS can be used to stimulate a cerebellar pathway connecting to a brainstem, a diencephalon, or a cerebrum to treat a range of different neurological conditions (e.g., stroke, epilepsy, movement disorders, psychiatric disorders, mood disorders, neurological deficits resulting from trauma/surgical treatment, demyelination, or neurodegeneration, or the like).

As used herein, the term "configure" when used with deep brain stimulation refers to choosing the electrode(s) to deliver the DBS and the parameters at which the DBS is to be delivered.

As used herein, the term "electrophysiology" refers to measurement of electrical activity associated with the nervous system. The electrophysiology measurement can be local to one or more parts of the nervous system.

As used herein, the term "local field potential", represented by the abbreviation LFP, refers to the electric potential recorded in the extracellular space in brain tissue. LFPs are an example of electrophysiology data.

As used herein, the term "electroencephalogram", represented by the abbreviation EEG, refers to signals from the brain recorded by external electrodes attached to the scalp (also referred to as EEG scalp electrodes).

As used herein, the term "motor task" refers to a movement or action of one or more muscles.

As used herein, the term "titration" refers to a process of configuring a stimulation to reduce symptoms to the greatest possible degree while avoiding as many side effects as possible.

As used herein, the term "optimal" refers to something that is the most favorable. For example, an optimal solution satisfies most or all conditions with no or a small number of negative results.

As used herein, the terms "user" and "patient" can be used interchangeably and refer to any warm-blooded organism that may be suffering from a neurological disorder that is treated with DBS.

As used herein, the term "medical professional" refers to any trained caregiver, such as a doctor, a medical student, a physician's assistant, a nurse, a technician, or the like.

II. Overview

Traditionally, deep brain stimulation (DBS) has been used on patients with movement disorders caused by neurological conditions like Parkinson's disease and essential tremor to minimize instances of the movement disorders. In these traditional uses of DBS, a medical professional can visually observe when the unwanted movement reduces, Thus, configuration of the DBS system involves the medical professional testing a series of settings and observing the corresponding improvement or worsening of symptoms of the unwanted movement. As the uses of DBS expand to treat different neurological disorders (e.g., stroke and its sequelae, weakness, epilepsy, cognitive disorders, movement disorders, psychiatric disorders, mood disorders, neurological deficits arising from trauma/surgical treatment, demyelination, neurodegeneration, or the like) by stimulating a cerebellar pathway connecting to a brainstem, a diencephalon, or a cerebrum, such conventional methods for selecting a stimulation configurations become unusable. As an example, the sequelae from stroke is one of many indications that can be treated with DBS of the cerebellothalamocortical (CTC) pathway, but configuring the DBS system for stroke patients by traditional means has proven difficult.

To overcome these challenges associated with configuring DBS to stimulate a cerebellar pathway connecting to a brainstem, a diencephalon, or a cerebrum to treat the neurological disorder in the patient, the present disclosure relates to systems and methods for configuring the DBS system based on biomarkers used to determine optimal stimulation patterns of the DBS on related neural networks (e.g., the cerebellothalamocortical pathways for stroke). The biomarkers are derived from one or more of the following electrophysiological and/or biomechanical techniques, including electrical stimulation of any component of a neural pathway associated with the neurological condition, internal recordings of electrophysiology of sub-cortical areas and/or deep brain tissue, external recordings of conduction from the primary motor cortex, secondary motor cortex, primary sensory cortex, and/or secondary sensory cortex, and mechanical measures when performing or attempting to perform at least one motor task with a task component that can provide a mechanical or digitized measurement of movement, including displacement/velocity/acceleration of an extremity or body part, dexterity of an extremity or body part, strength of an extremity or body part, resistance, including rigidity or spasticity, of an extremity or body part, and electromyography. Described herein is the use of several of these biomarkers to configure a DBS system to stimulate a cerebellar pathway connecting to a brainstem, a diencephalon, or a cerebrum of a patient to treat a certain neurological disorder in a patient. Specifically internal recordings of electrophysiology data, external recordings of EEG data, and mechanical measures. It should be noted that the other biomarkers can be used as necessary to accomplish this configuration of the DBS system for the patient.

III. Systems

An aspect of the present disclosure can include a system 10 (FIG. 1) that can be used to configure a DBS system to stimulate a cerebellar pathway connecting to a brainstem, a diencephalon, or a cerebrum of a patient to treat a neurological disorder in the patient. The system can include a controller 12 that receives (1) internal 13 data from a neurostimulator 14 (which can be internal to the body and/or external to the body) regarding data recorded by one or more implanted DBS electrodes 15 and (2) external 16 data from one or more EEG scalp electrodes 16 in response to a patient performing a motor task with a task component 18. The controller 12 can include one or more output devices 19 to give instructions to the patient and/or medical professional and/or to provide an output configuration for the DBS system.

It should be noted that the internal 13 portion is implanted in a patient—with the DBS electrodes 15 in the patient's brain and the neurostimulator being remote from the brain (either external to the body or implanted under the patient's skin)—and the external 16 portion is not implanted in the patient. The external EEG scalp electrodes are illustrated as a plurality of electrodes, but should be understood as including any number of electrodes that is limited by the size of the patient's head and greater than one. Additionally, it should be understood that the components of FIG. 1 are not to scale and not shown in their normal positions.

At least one of the components of FIG. 1 (e.g., at least controller 12) can be equipped with a non-transitory memory storing instructions for the configuration (and in some instances data) and a processor to access the non-transitory memory and execute the instructions. The non-transitory memory and the processor can be implemented as a single circuit, such as an application specific integrated circuit (ASIC), but may be in any possible implementation of a non-transitory memory and an associated processor. An input device, such as a mouse or a keyboard, can be a component of controller 12 to allow interaction with the controller 12 or any other component the system 10.

The controller 12 can engage in wired and/or wireless communication. For example, the controller 12 can communicate with the neurostimulator 14 that is implanted internal 13 to the patient's body according to a near field wireless communication means (with any necessary additional circuitry not illustrated). The external EEG scalp electrodes can be connected to the controller (through means that may not be illustrated) to engage in wired communication. The controller 12 can be connected to the task component 18 and/or the output device 19 according to a wired or wireless connection.

The task component 18 can be one or more instruments configured to measure one or more mechanical properties of performing a task that the user has been instructed to perform. As an example, the task component 18 can provide a mechanical or digitized measurement of movement and can include a dynameter, digital plate, articulated lever, robotic arm or other mechanical or digitized measurement of movement. This measurement of movement can include, for example, displacement/velocity/acceleration of an extremity or body part, dexterity, strength, resistance (rigidity or spasticity), electromyography, etc. of an extremity or body part.

Figure 4:
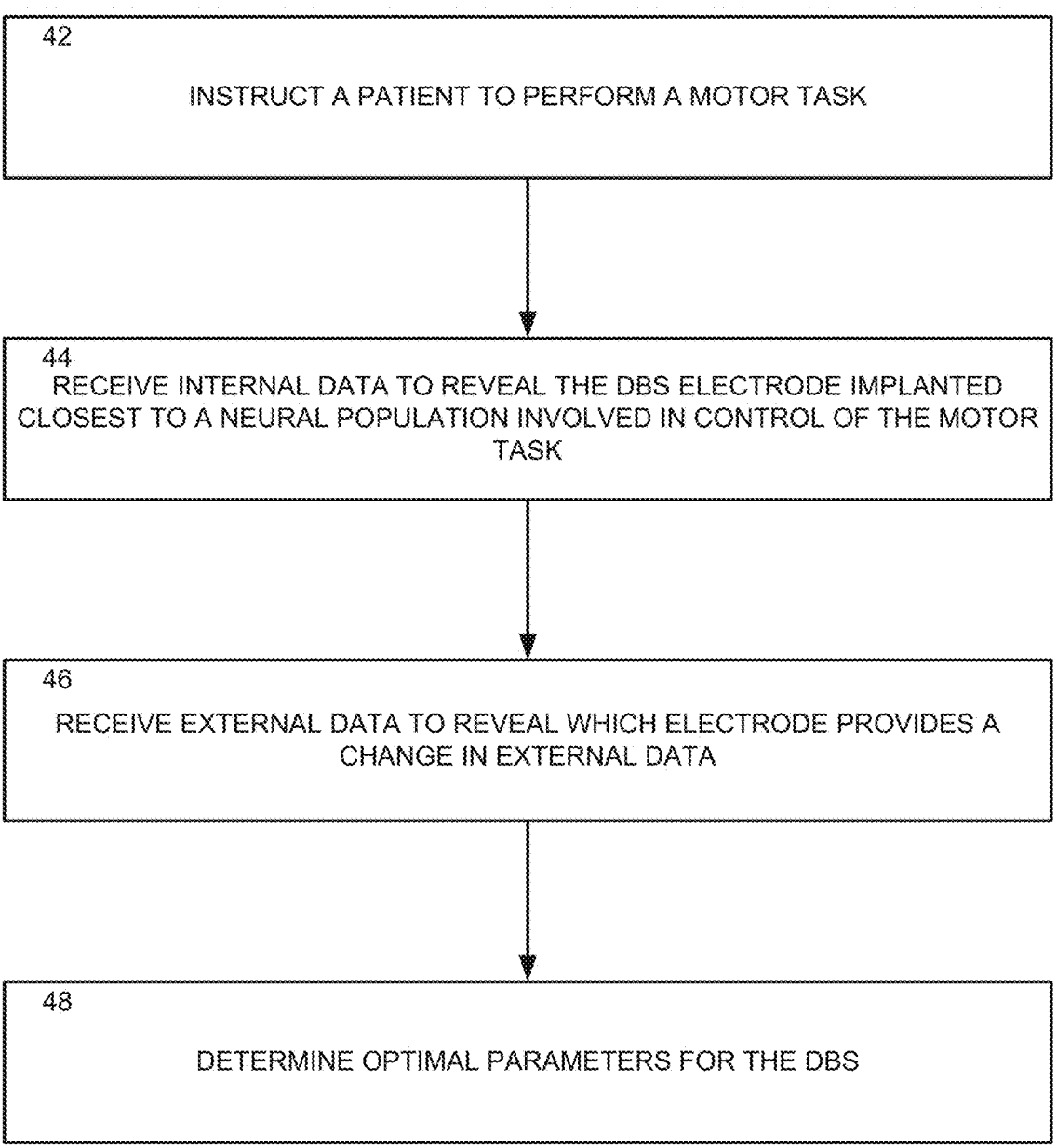
FIG. 4 is a process flow diagram illustrating a method for configuring a DBS system to stimulate a cerebellar pathway connecting to a brainstem, a diencephalon, or a cerebrum of a patient to treat a neurological disorder in the patient in accordance with another aspect of the present disclosure.

The system 10 can be used to configure a DBS system to stimulate a cerebellar pathway connecting to a brainstem, a diencephalon, or a cerebrum of a patient to treat a neurological disorder in the patient. The controller 12 can perform steps related to the configuration, including one or more of: electrical stimulation of any component of a neural pathway associated with the neurological condition, internal recordings of electrophysiology of sub-cortical areas and/or deep brain tissue, external recordings of conduction from the primary motor cortex, secondary motor cortex, primary sensory cortex, and/or secondary sensory cortex, and mechanical measures when performing or attempting to perform at least one motor task with a task component. For example, the system 10 can be used to execute the process 40 (FIG. 4) described below (or any other process for configuration that uses a different combination of electrical stimulation of any component of a neural pathway associated with the neurological condition, internal recordings of electrophysiology of sub-cortical areas and/or deep brain tissue, external recordings of conduction from the primary motor cortex, secondary motor cortex, primary sensory cortex, and/or secondary sensory cortex, mechanical measures when performing or attempting to perform at least one motor task, or the like).

Figure 2:
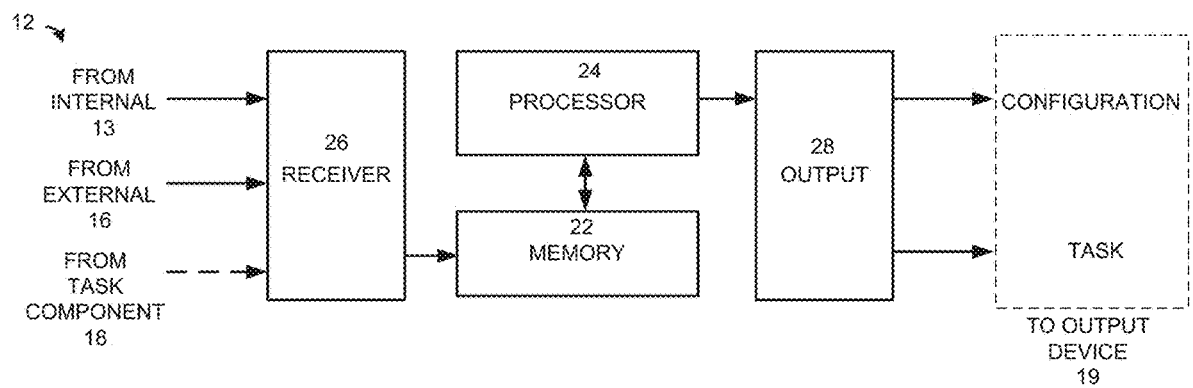
FIG. 2 shows example inputs and outputs to the controller of FIG. 1.

As shown in FIG. 2, the controller 12 can have a non-transitory memory 22 storing instructions and data and a processor 24. For example, the non-transitory memory can be a read only memory (ROM), random access memory (RAM), magnetic RAM, core memory, magnetic disk storage medium, optical storage medium, flash memory device, and/or other machine readable mediums (readable by the processor, in other words) for storing information, including instructions and/or data. The non-transitory memory 22 can be associated with a receiver 26. The processor 24 can be associated with an output 28.

Figure 3:
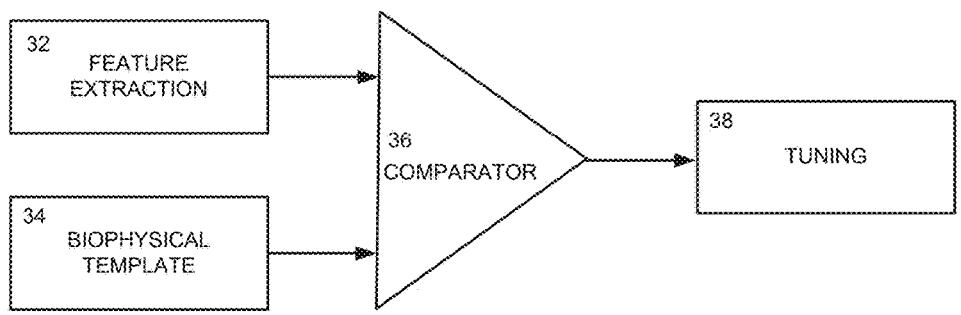
FIG. 3 shows an example of how the controller can use tuning to configure the DBS system.

The receiver 26 can receive signals from the internal 13 portion and the external 16 portion that include internal data (e.g., electrophysiology data) and external data (e.g., EEG data). In some instances, the receiver 26 can also receive data from the task component 18, such as information related to one or more mechanical properties of performing a task that the user has been instructed to perform. The processor 24 can use at least a portion of the data received and provide an output (including a configuration, a task, or the like) to the output 28. The output 28 can provide the output to be output device 19, which can provide an audio and/or visual output. For example, as shown in FIG. 3, the processor 24 can execute the comparison 30 between one or more features extracted from one or more of the signals (feature extraction 32) and one or more templates (biophysical template 34) can be compared by the comparator 36 and based on the comparison, the parameters of the DBS stimulation can be tuned 38. The tuned parameters can be output by the output 28.

IV. Methods

Another aspect of the present disclosure can include a method 40 (FIG. 4) for configuring a deep brain stimulation (DBS) system to stimulate a cerebellar pathway connecting to a brainstem, a diencephalon, or a cerebrum of a patient to treat a neurological disorder in the patient. The method 40 can be executed using the system 10 shown in FIG. 1 (with further aspects shown in FIGS. 2 and 3).

For purposes of simplicity, the method 40 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 40, nor is the method 40 necessarily limited to the illustrated aspects. Additionally, one or more of the steps can be stored in a non-transitory memory and accessed and executed by a processor.

As an optional first step (not shown), an initial monopolar review (or electrical stimulation) can occur to determine any electrode(s) and/or stimulation parameters that cause undesirable side effects. These electrode(s) and/or stimulation patterns can be excluded from the further steps of the method 40. The decision to exclude can be specific to the user (e.g., based on symptoms and/or the way the electrodes are implanted). However, the decision to exclude may be based on (or supplemented by) data specific to a population that includes at least one similar patient.

At Step 42, a patient can be instructed to perform one or more motor task. For example, the patient can be instructed to perform the one or more motor task by a medical professional (e.g., chosen from predefined motor tasks based on the medical condition of the patient). As another example, the controller (element 12 of FIG. 1) can determine the one or motor tasks (based on data input about the patient and/or past performance of the patient and/or a population of similar patients) and output the instruction related to the one or more motor tasks by audio and/or video (e.g., by output device 19 associated with controller 12). In response, the patient can perform, at least attempt to perform, or even think about performing the one or more motor task as internal data (e.g., electrophysiology data used in Step 44 and/or external data (e.g., electroencephalography (EEG) data used in Step 46 can be recorded by appropriate electrodes and received (by controller 12). In some instances, the motor task can be aided by a task component (element 18 of FIG. 1) that can also record data related to the motor task.

One or more electrodes are selected to deliver the stimulation by a combination of Step 44 and Step 46. These steps can occur in any order. Additionally, although described as related to the patient performing or attempting to perform the same motor task, it will be understood that the Steps can occur with multiple motor tasks, which are either the same or different. For example, the motor task can include moving an affected extremity, such as an arm, a hand, a finger, a foot, or a leg. In some patients, different parts of the same extremity may be affected and/or different extremities may be affected.

At Step 44, internal data (which can be electrophysiology data recorded/measured by implanted DBS electrodes 15 during the task, e.g., local field potential (LFP) recordings by implanted DBS electrodes measured) can be received/analyzed (by controller 12). The internal data can reveal which electrode(s) (of the DBS electrodes 15) has a strongest signal recorded based on the the motor task. The strength of the signal can be indicated in by a power in a theta, alpha, beta, and/or gamma oscillatory band and/or a power change in an theta, alpha, beta, and/or gamma oscillatory band of each electrophysiology signal (e.g., LFP signals). The DBS electrodes (DBS electrodes 15) can be implanted in at least one cerebellar pathway connecting to a brainstem, a diencephalon, or a cerebrum. Based on the electrophysiology data, at least one of the electrodes can be identified as implanted closest to a neuronal populations involved in control of the at least one motor task.

At Step 46, external data (which can be EEG data recorded by at least one external EEG scalp electrodes-a plurality of external EEG scalp electrodes are shown as element 17 of FIG. 1) can be received/analyzed (by controller 12). For example, the EEG scalp electrodes (element 17 of FIG. 1) can be located over the user's primary motor cortex, secondary motor cortex, primary sensory cortex, and/or secondary sensory cortex. The external data can reveal which electrode provides a change in the external data. For example, the change in the EEG data can be a change in event related desynchronization (ERD) and/or event related synchronization (ERS) and/or may be seen in theta, alpha, beta, and/or gramma band activity in the EEG data. Based on the EEG data, at least one of the electrodes can be identified as causing the change.

The electrode(s) identified as closest to the neuronal populations in control of the at least one motor task and the electrode(s) identified as causing the change can be compared and the ideal electrode to deliver the DBS can be chosen. In some instances, the electrode(s) identified as closest to the neuronal populations in control of the at least motor task can be identified and the electrode(s) identified as causing the change can be narrowed down to the ideal electrode(s). However, in other instances, the electrode(s) identified as closest to the neuronal populations in control of the at least motor task and the electrode(s) identified as causing the change can be weighed against one another to select the ideal electrode(s). It should be noted that the electrode(s) identified as closest to the neuronal populations in control of the at least motor task and the electrode(s) identified as causing the change may be compared in different ways to select the electrode(s) to deliver the DBS stimulation or different data may be used additionally—e.g., in some instances, a change in an instrumentation-based motor behavior while performing the task can be additionally considered in the weighting.

At Step 48, the optimal parameters for the DBS can be determined. In some instances, the optimal parameters are parameters that provide a response indicative of modulation with a lowest magnitude. For example, the optimal parameters comprise an optimal stimulation amplitude, one or more optimal burst parameters, an optimal stimulation frequency, and an optimal stimulation pulse width.

The optimal parameters for the DBS and the at least one of the potential stimulation electrode to deliver the DBS can be output (e.g., by the controller 12 to output device 19) for guiding configuration of the DBS system for the user. In some instances, these optimal parameters and ideal electrodes selected are presented as a check or guide for the medical professional (e.g., the medical professional can try the optimal parameters and ideal settings first). However, in other instances the configuration can be done in an automated fashion.

V. Experimental

The following example shows the use of an example of the integrated approach to configure a deep brain stimulation (DBS) system according to biomarkers, as described herein.

As new treatments are developed based on deep brain stimulation for neurological disorders like stroke and other non-traditional DBS targets, new challenges arise related to configuring the DBS system in that the configuration can no longer rely on acute observations to select ideal electrical stimulation parameters because no acute improvements are improved during programming. Instead, biomarkers are needed that will change acutely in response to different electrical stimulation settings and will predict the long-term outcome adequately.

A first-ever clinical trial of DBS targeting the cerebellar pathways connecting to the cerebral cortex is being conducted with an objective of enhancing the outcomes of post stroke rehabilitation and improving the patient's quality of life. From this study, data has been collected that corroborates the feasibility of this intervention and indicates the identification of some of such biomarkers to facilitate configuring and programming of the DBS system.

As shown in FIG. 5, the approach for configuring the DBS system includes: (1) conduct a monopolar review to narrow down possible therapeutic settings, excluding those that cause acute side effects such as sensation of pulling, motor changes or any other undesired symptom (step 52—electrode causes side effects? This step is optional.); (2) use information gained from electrophysiology (e.g., local field potentials (LFPs)) measured from the DBS electrodes during tasks, such as moving or attempting to move the arm, hand, fingers, foot or leg, which indicates electrodes that are implanted closest to the neuronal populations mostly involved in motor control and helps select the best electrodes for stimulation out of the multi-electrode leads (step 54—local effects?); (3) test for acute effects of DBS settings on the perilesional cortex or contralesional cortex using scalp electroencephalography (EEG) measures such that DBS settings are selected or refined based on which settings provide the most robust changes in event-related desynchronization and event-related synchronization (ERD and ERS), another indicator of which electrodes from the multi-electrode lead are best for stimulation (step 56—acute effects?); (4) in some instances, combined with the EEG measurements, results of motor behavioral tasks that can indicate the motor performance with greater accuracy and precision than simple naked-eye observation (e.g., motor speed, grip or extension strength, dexterity, and the like) can be used to further configure the DBS system (optional, may be part of step 56—acute effects?); and (5) stimulation parameters can be optimized (step 58—titrate). The intent is to select the lowest amplitude that produces a robust response on the perilesional cortex, indicative of modulation. Higher amplitudes that produce similar results are seen as less desirable as they increase the likelihood of side effects without increments in modulation. The following data is shown related to step (2) (FIGS. 6-8), step (3) (FIG. 9), step (4) (FIG. 10), and step (5) (FIG. 11).

Step (2)

FIGS. 6-9 show LFPs recorded from DBS electrodes. This data shows modulation of LFPs recorded from the cerebellar dentate nucleus during performance of a motor task using the effected extremity.

Figure 6:
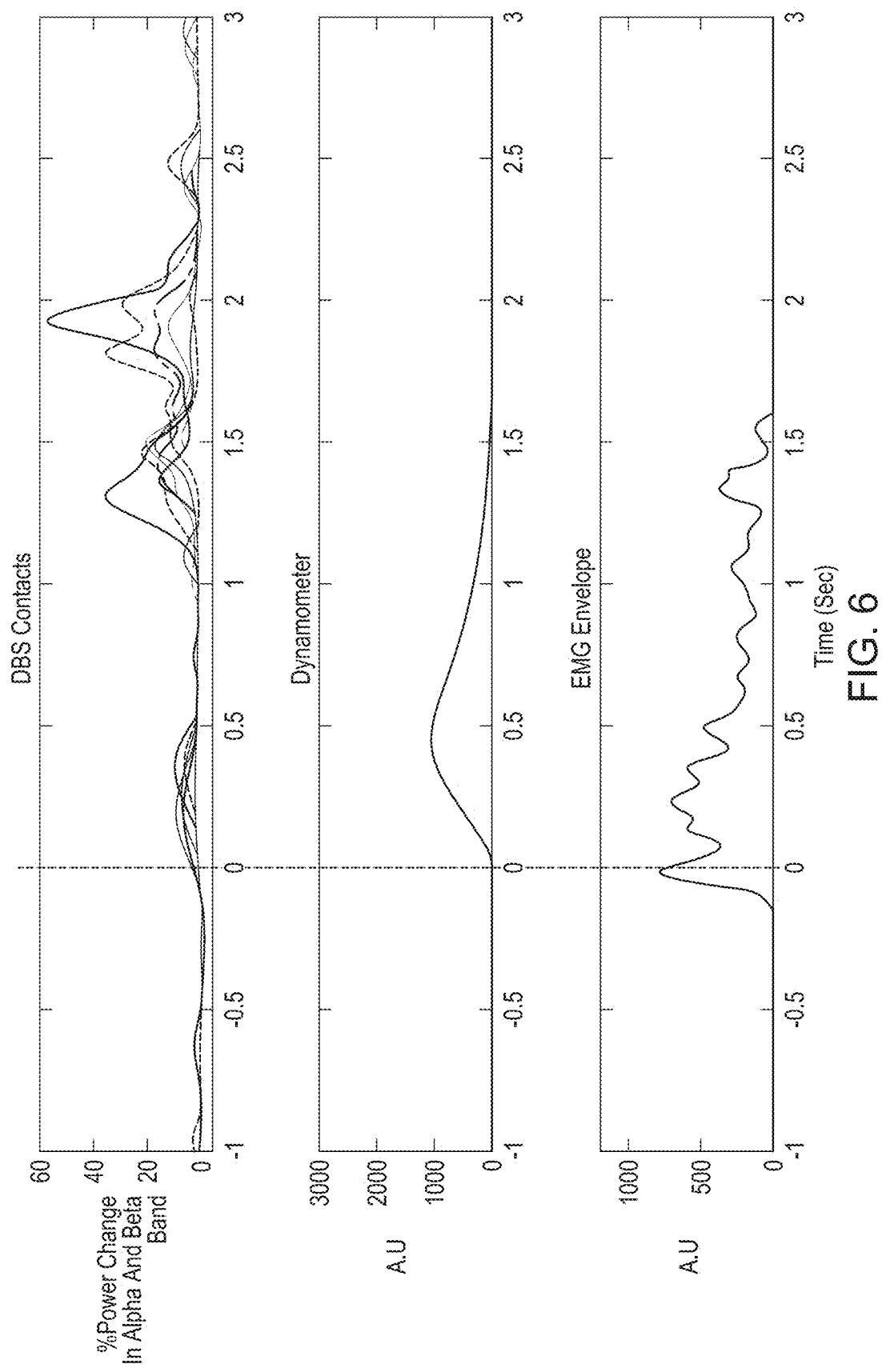
FIG. 6 shows modulation of local field potentials (LFPs) recorded from the cerebellar dentate nucleus during performance of a motor task using an affected extremity.

FIG. 6 shows the overall change in alpha and beta band power from LFP (top row), the dynamometer force (middle row), and EMG envelope recorded from muscles (bottom row) profile during a motor squeeze task. The x-axis in all rows is time in seconds for all rows. For the top row, the y-axis represents the amount of power present in the LFP signal that falls within the traditionally-defined alpha and beta oscillatory bands.

Time 0 is the onset of force production. As depicted, although there was a modest, initial increase in LFP power during force production, the largest modulation in LFP was observed during squeeze relaxation starting at approximately one second after force onset. Note the significant change in power in the beta and alpha bands that occur when the patient attempts to relax the hand, as shown by the reduction in activity from the dynamometer and the EMG.

Figure 7:
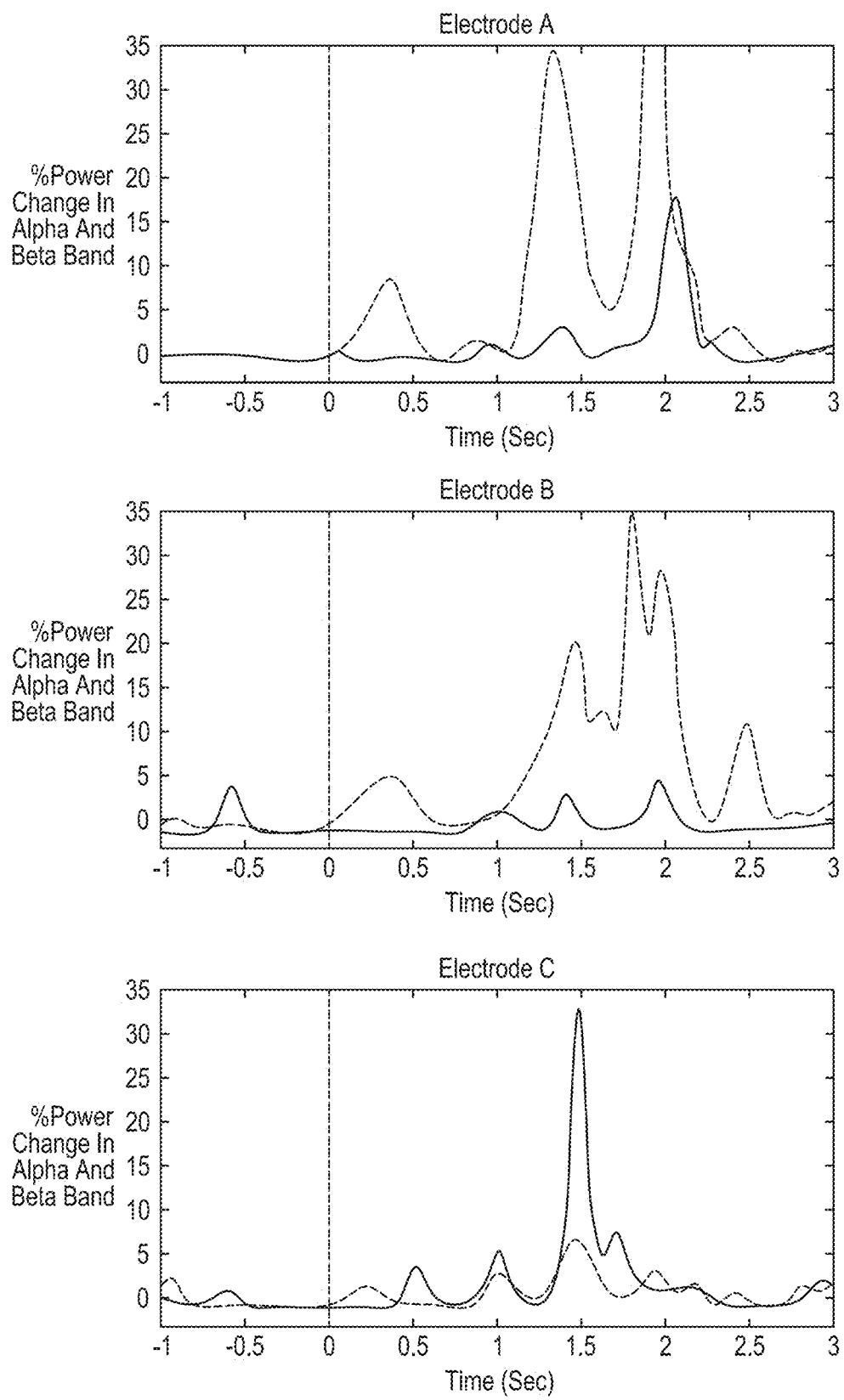
FIGS. 7 and 8 show modulation of LFPs for different electrodes in different patients.
Figure 7:
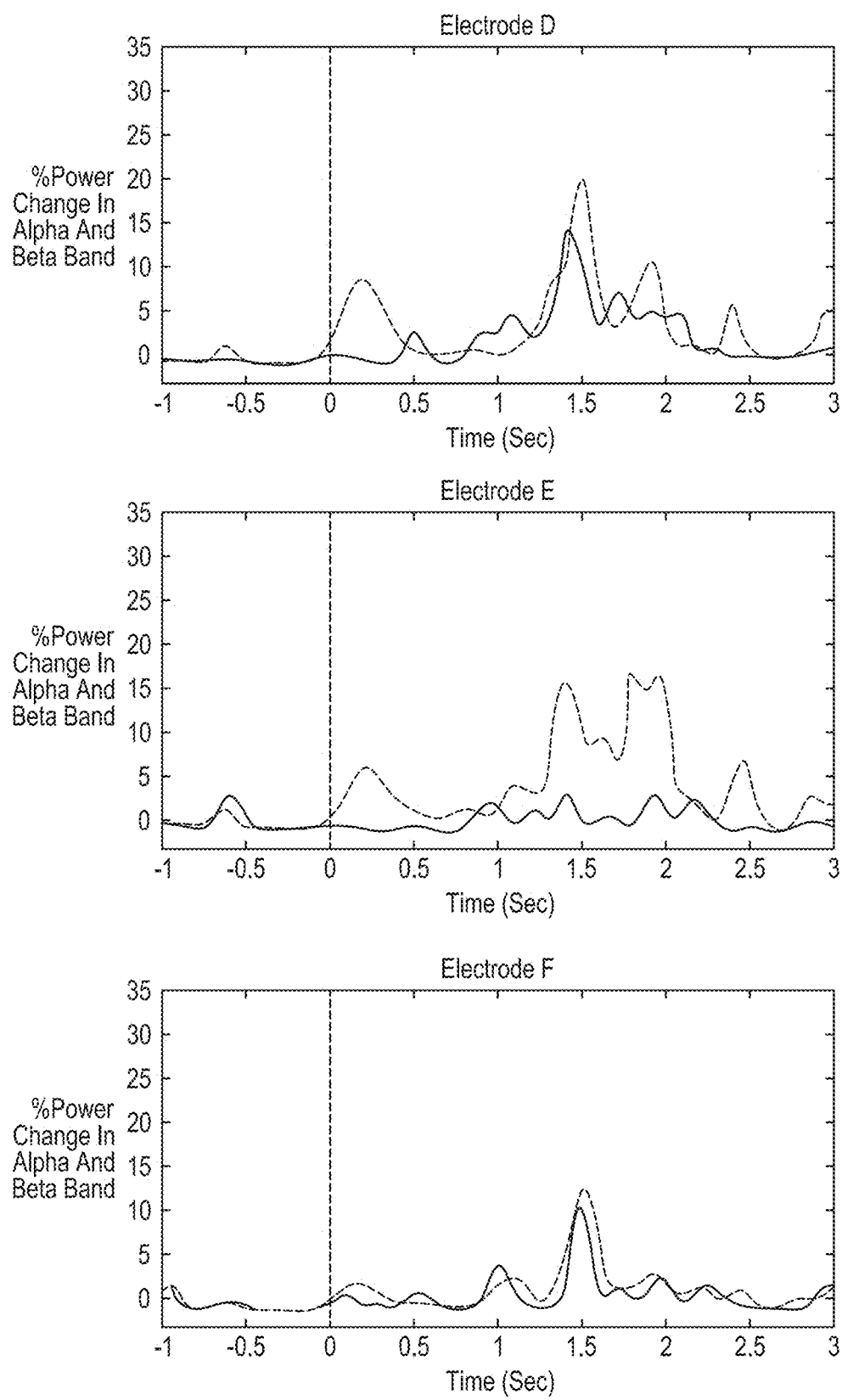
Figure 7:
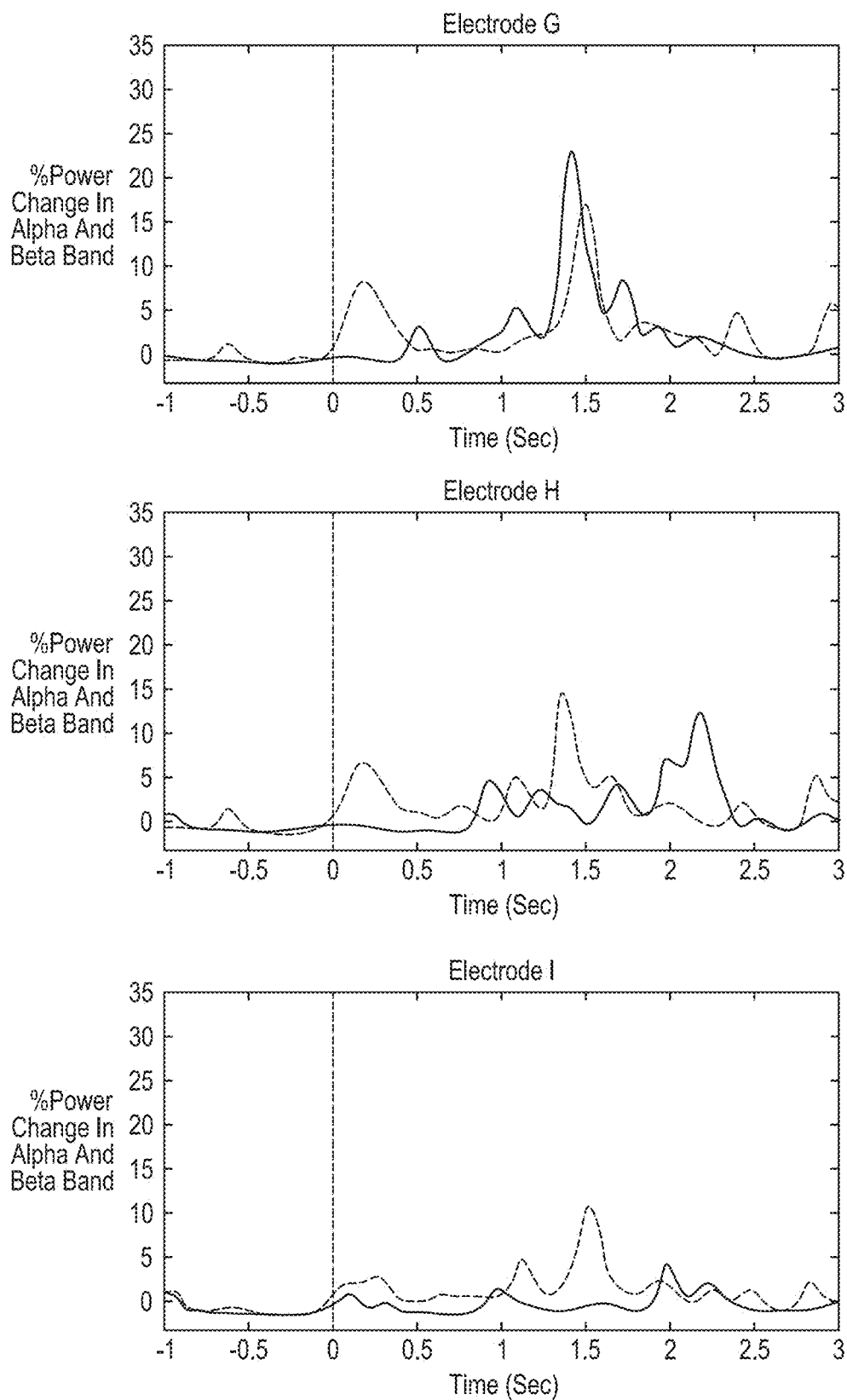
Figure 8:
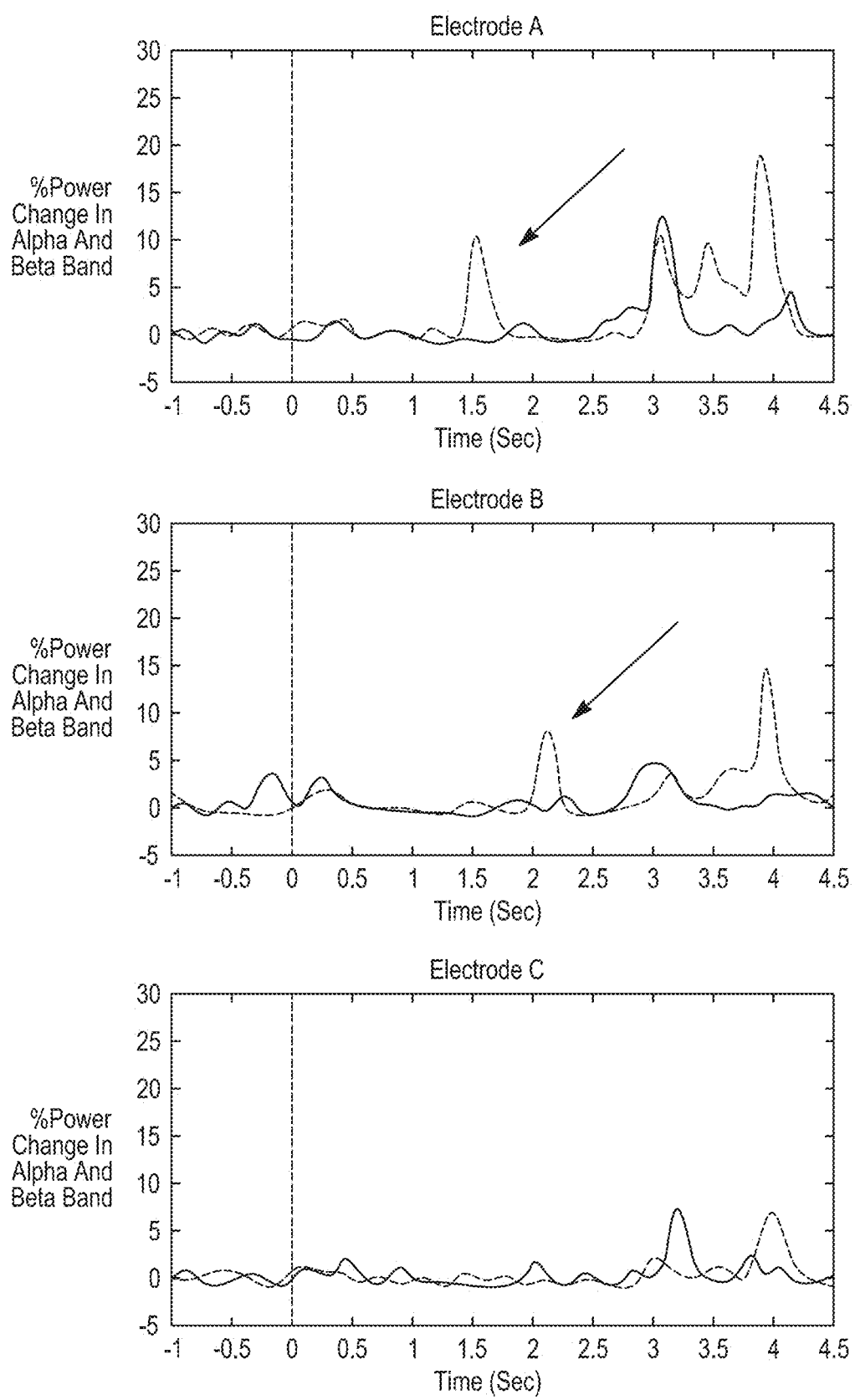
Figure 8:
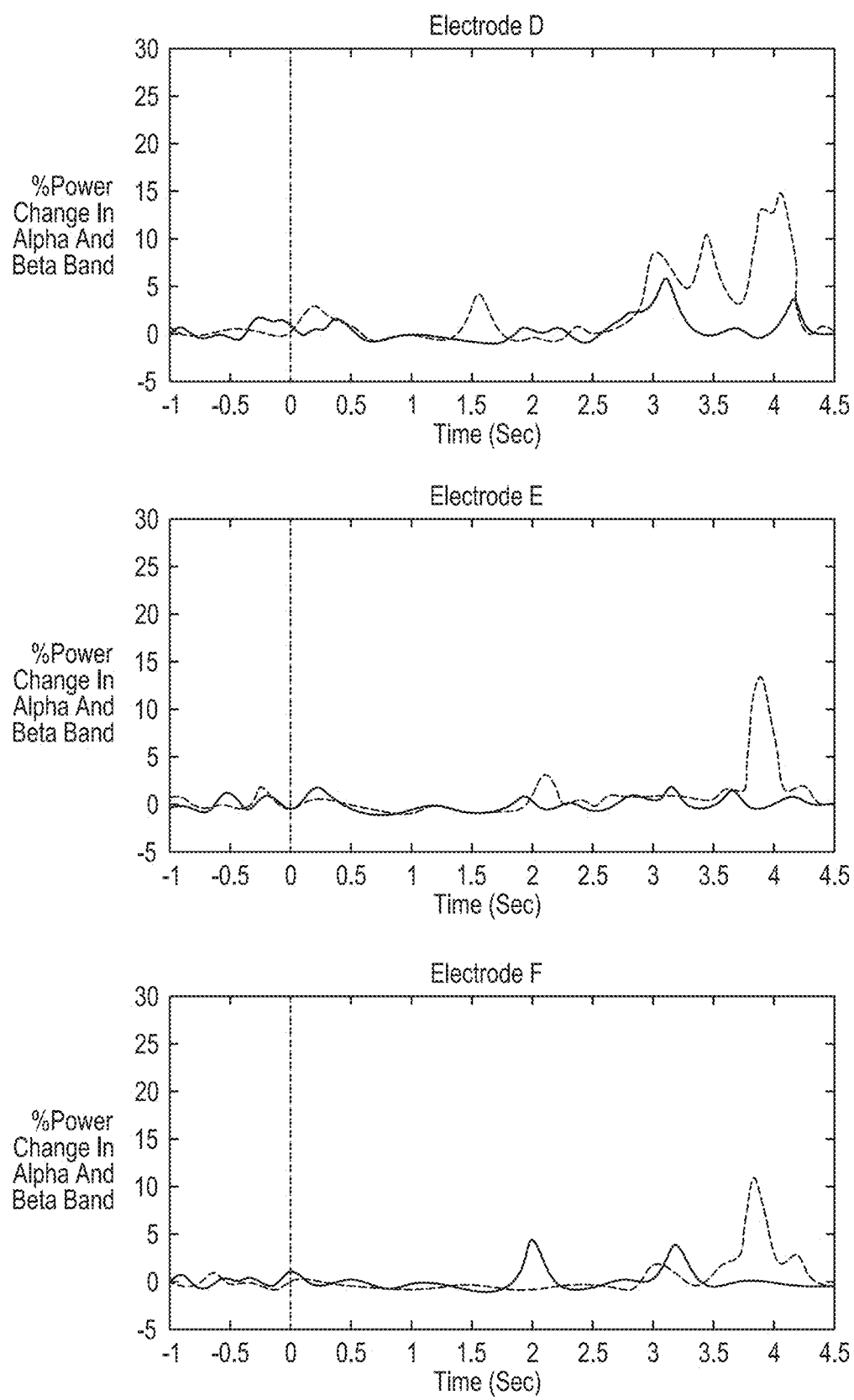
Figure 8:
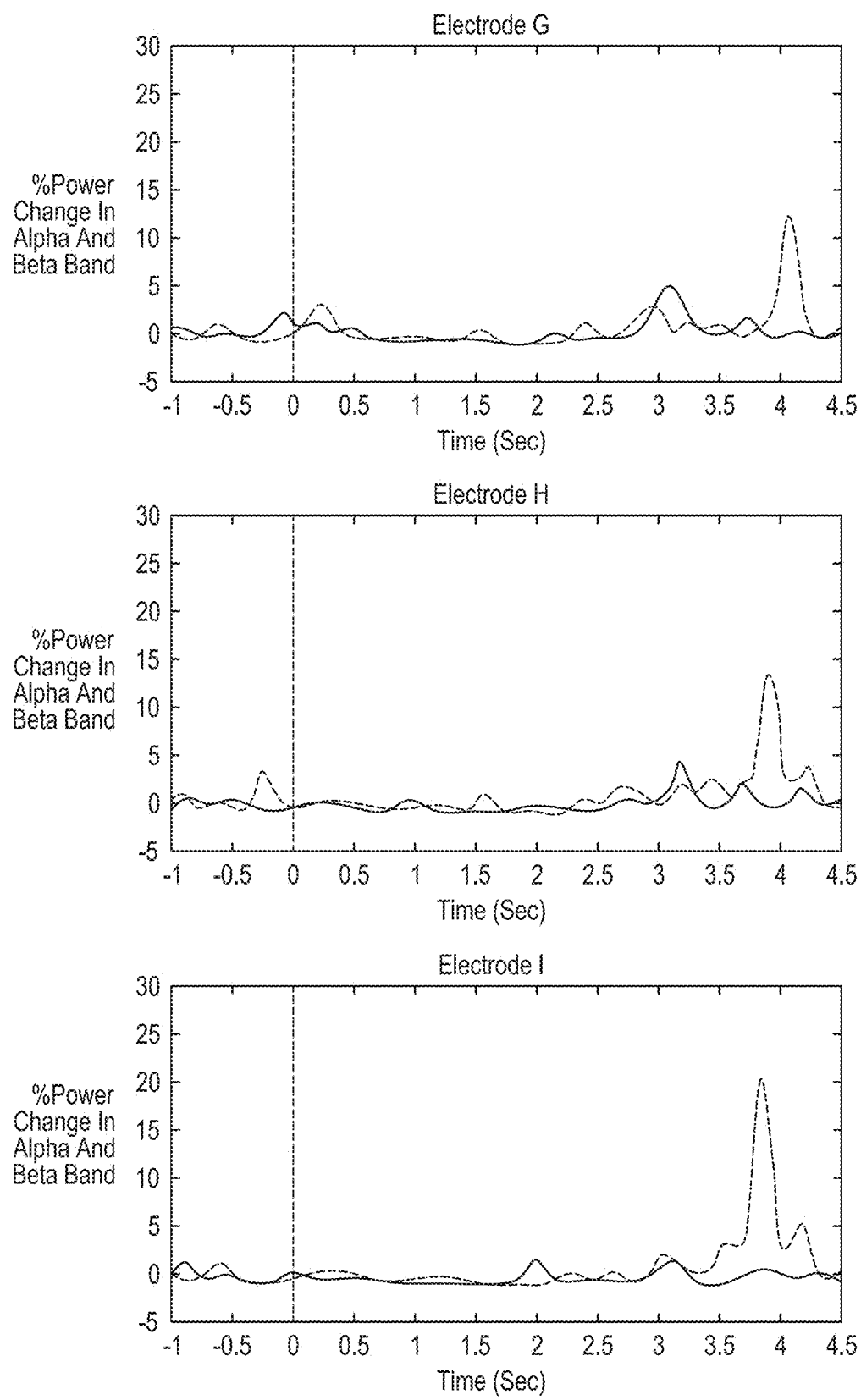

FIGS. 7 and 8 provide an assessment of which specific electrodes are recording the most significant changes in activity for two different patients. This is in addition to the overall changes in alpha and beta band activity shown in FIG. 6. In FIG. 7, the LFP modulation is plotted separately for each contact pair (there are 8 contacts in the electrode that was used) when affected (light colored line) and non-affected (dark colored line) upper extremities performed a motor task. Robust modulation was seen during tasks with the upper extremity affected by the stroke in DBS contacts A and B, but not in other contacts, suggesting that A and B are the best contact choices for long-term stimulation. FIG. 8 shows another example of strong activity occurring at the time of movement with upper extremity affected by stroke. Similar to the patient in FIG. 7, for the patient in FIG. 8, the most robust modulation was seen with contacts A and B.

Step 3

Figure 9:
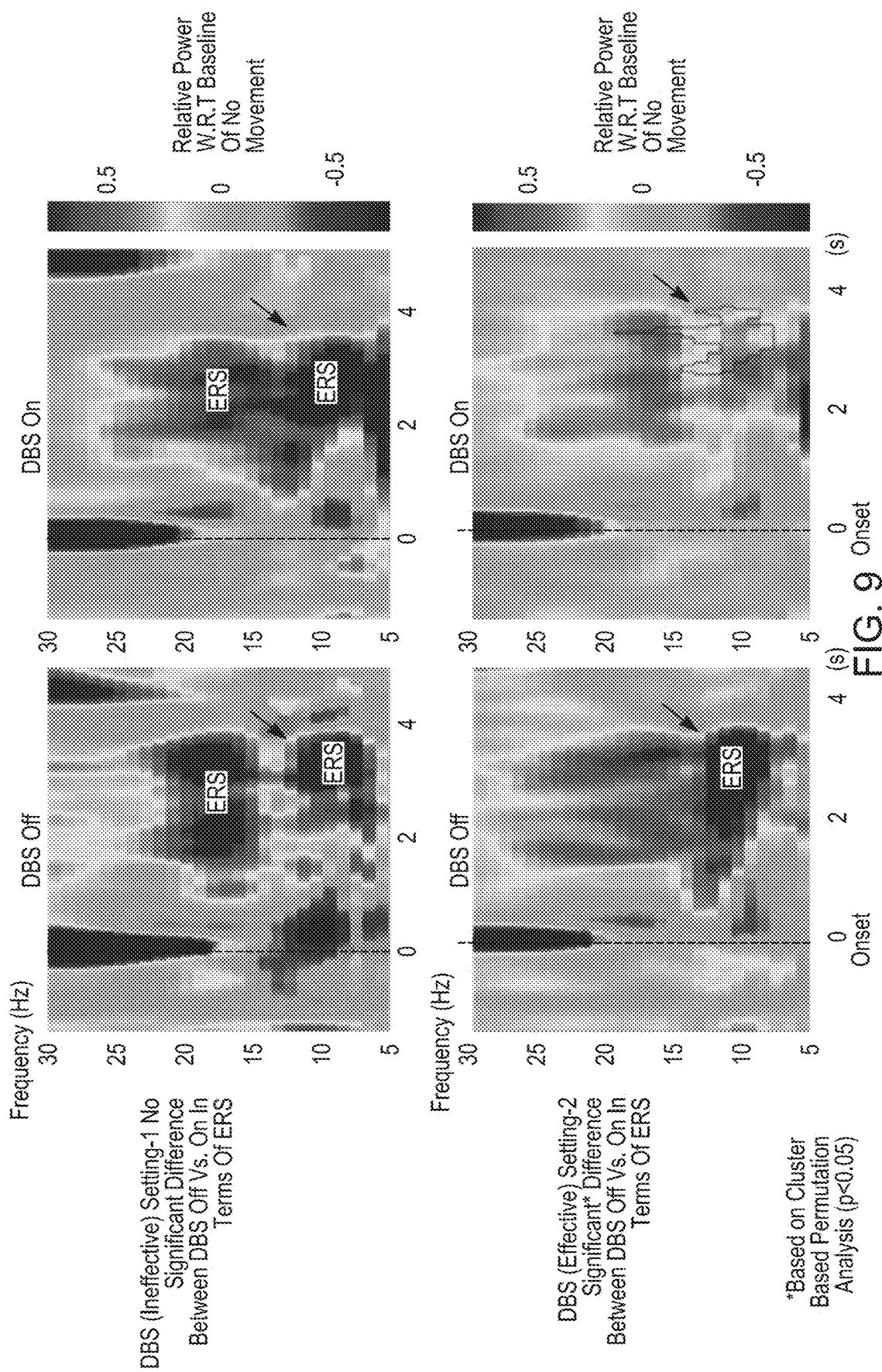
FIG. 9 shows task-related changes and DBS treatment related changes in alpha and beta band activity recorded using scalp electroencephalogram (EEG) electrodes placed over the contralateral sensorimotor cortex.

The possible DBS settings identified in Step (2) (and Step (1) if used) can be further tested in Step (3). FIG. 9 shows the acute effects of DBS on scalp EEG metrics. Specifically, task-related changes in the alpha (8-12 Hz) and beta (13-30 Hz) band activity can be recorded using scalp EEG electrodes placed over the contralateral sensorimotor cortex. Typically, task onset is marked by a transient change in power across the alpha/beta bands (event-related desynchronization (ERD)) followed by a rebound change of that power upon task completion (event-related synchronization (ERS)). These two phenomena have been shown to correlate with motor performance.

Subjects performed motor task with DBS switched OFF and turned ON with one or more of the candidate DBS settings identified. Comparing the ERD/ERS magnitude between DBS OFF and ON conditions will provide information about the ability of DBS to modulate cortical excitability. FIG. 9 shows Time-Frequency plots derived from time-series recorded using an EEG electrode over the perilesional cortex. The DBS setting for the top row is ineffective (e.g., the setting did not modulate ERS over perilesional cortex), while that in the lower row is considered to be effective (e.g., the setting successfully modulated ERS amplitude in a fashion consistent with movement facilitation).

Step 4 (Optional)

In addition to testing acute effects of DBS on EEG based metrics, significant improvements in motor behavior or metrics can be investigated. Of note, these are not naked-eye observations as typical of DBS programming for movement disorders. Rather, they are instrumentation-based, quantitative, objective metrics of motor function.

Figure 10:
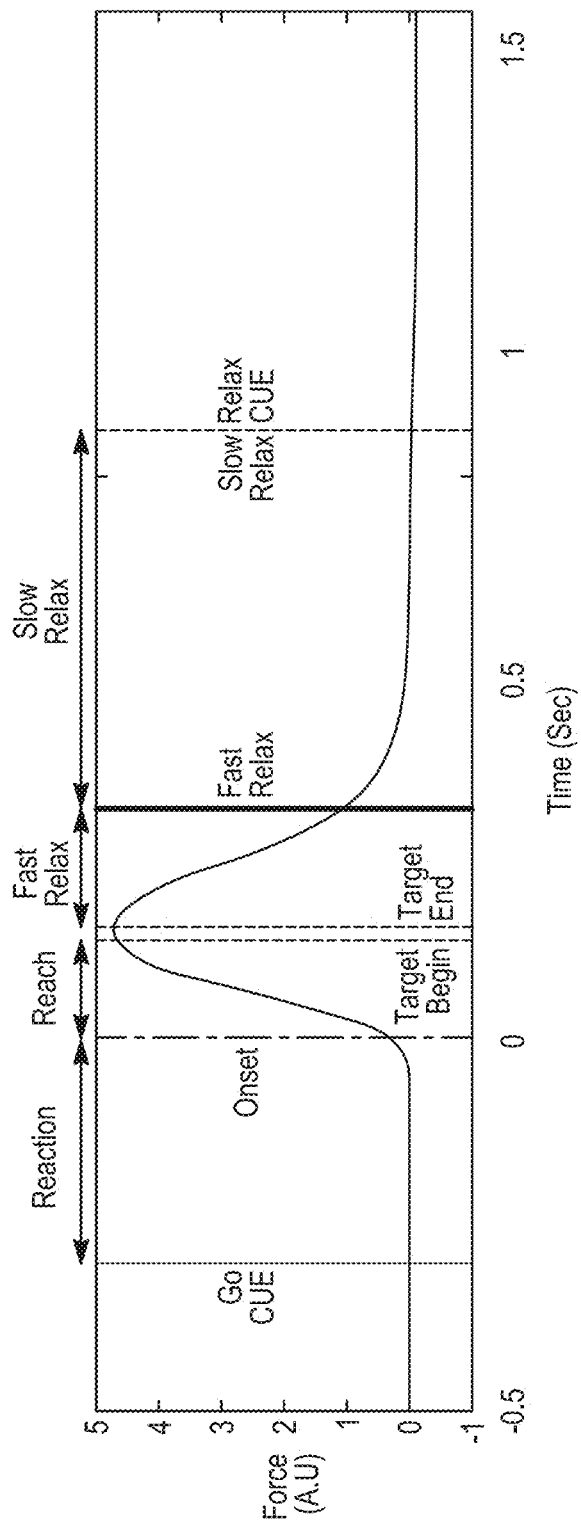
FIG. 10 shows different changes that occur in motor behavior or metrics.
Figure 10:
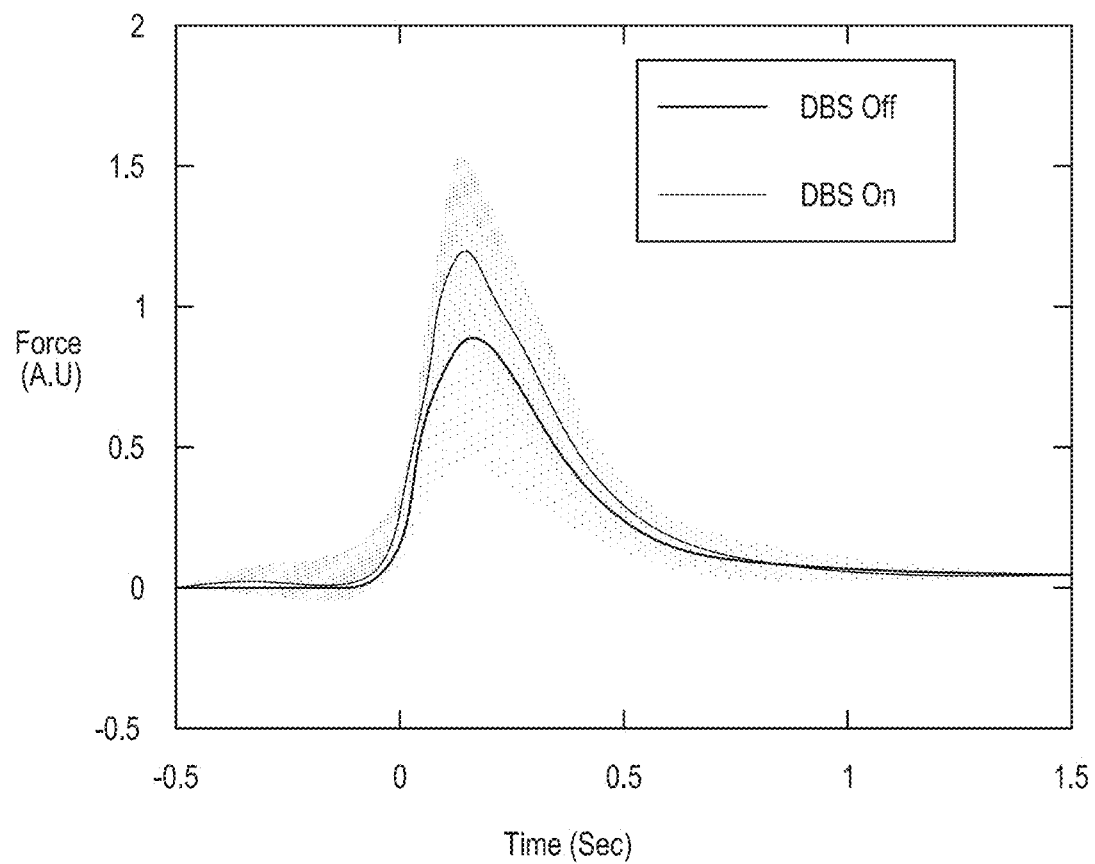
Figure 10:
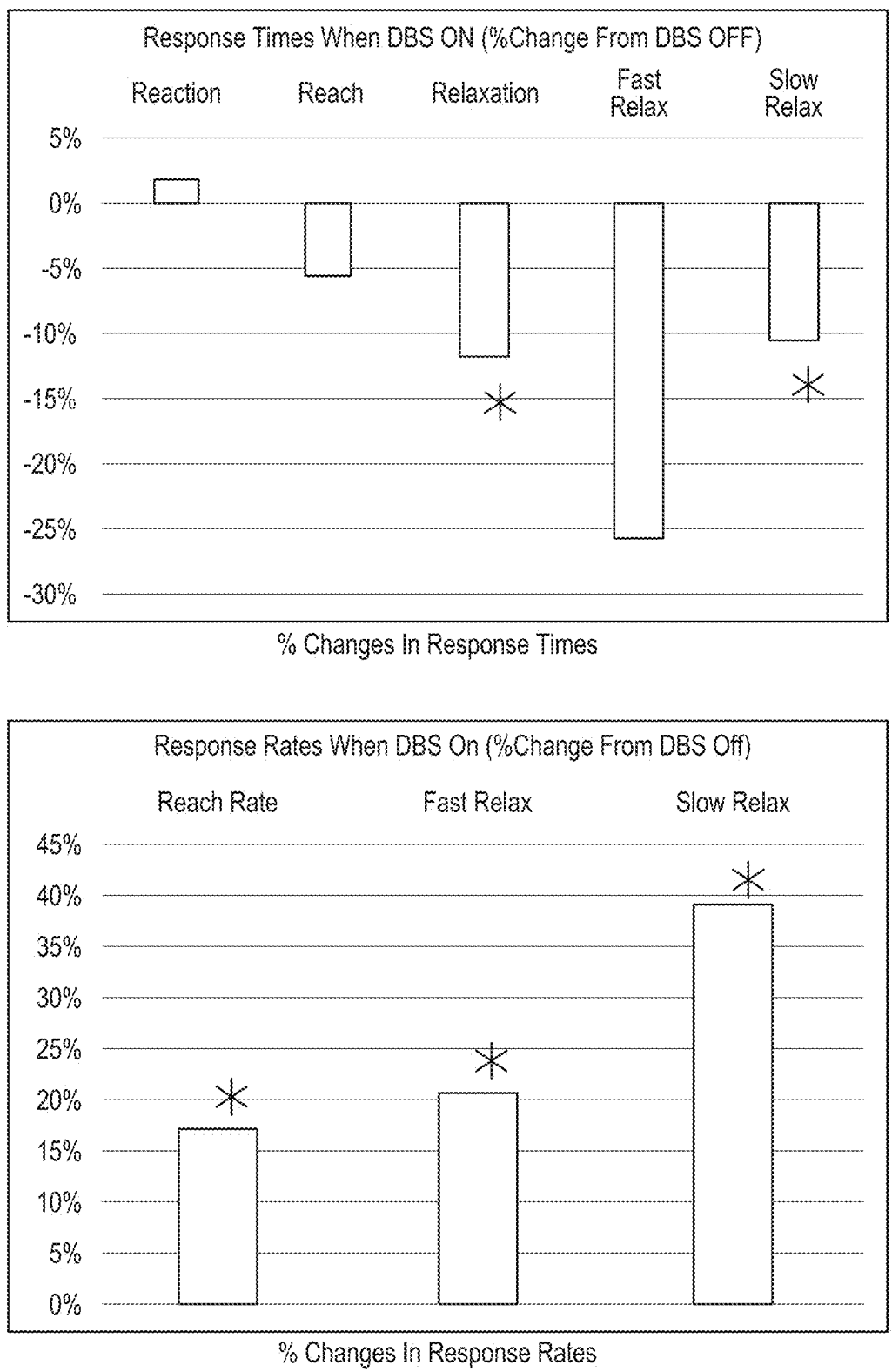
Figure 11:
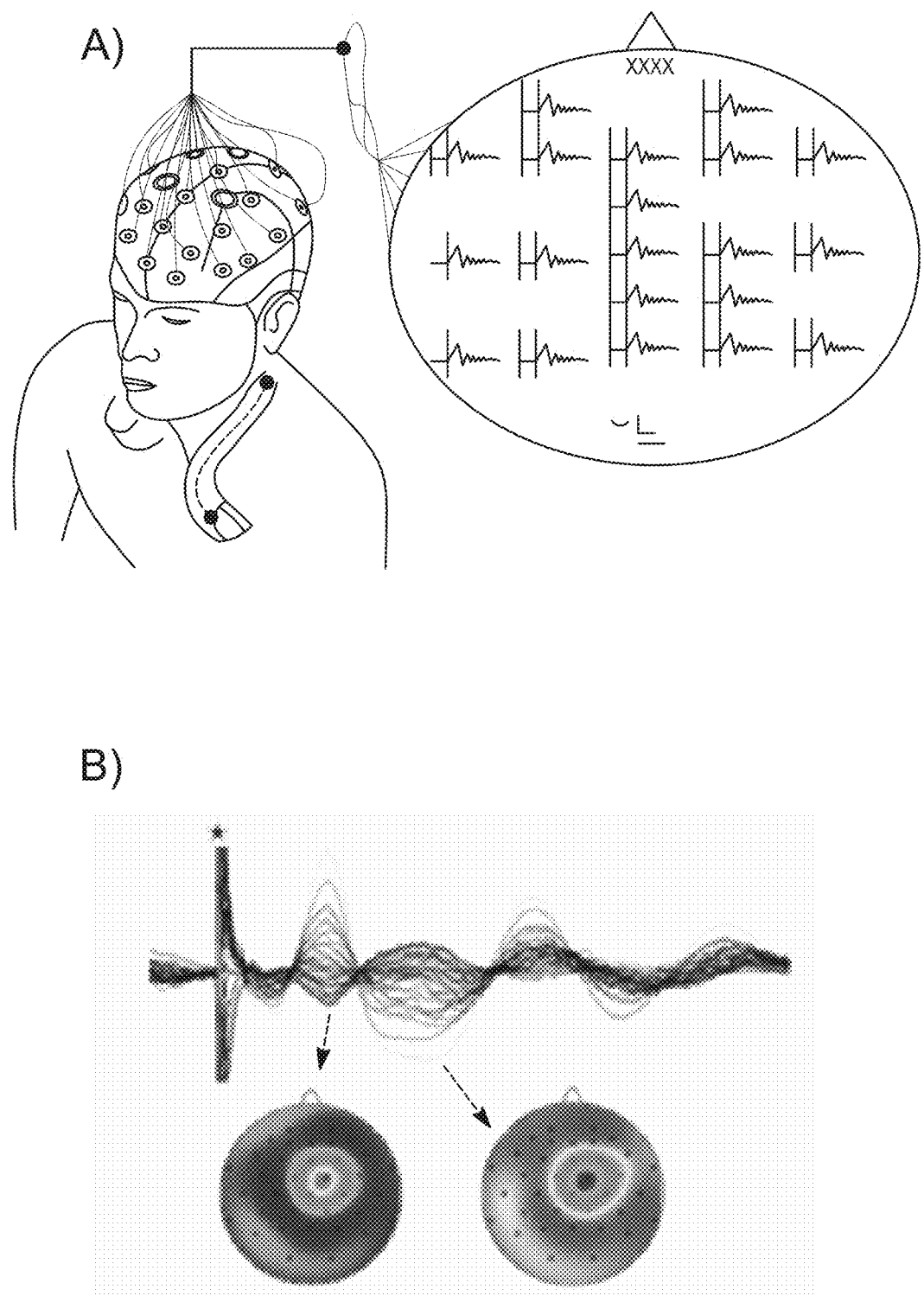
FIG. 11 shows the effects of titration to choose some of the parameters of the DBS system.
Figure 11:
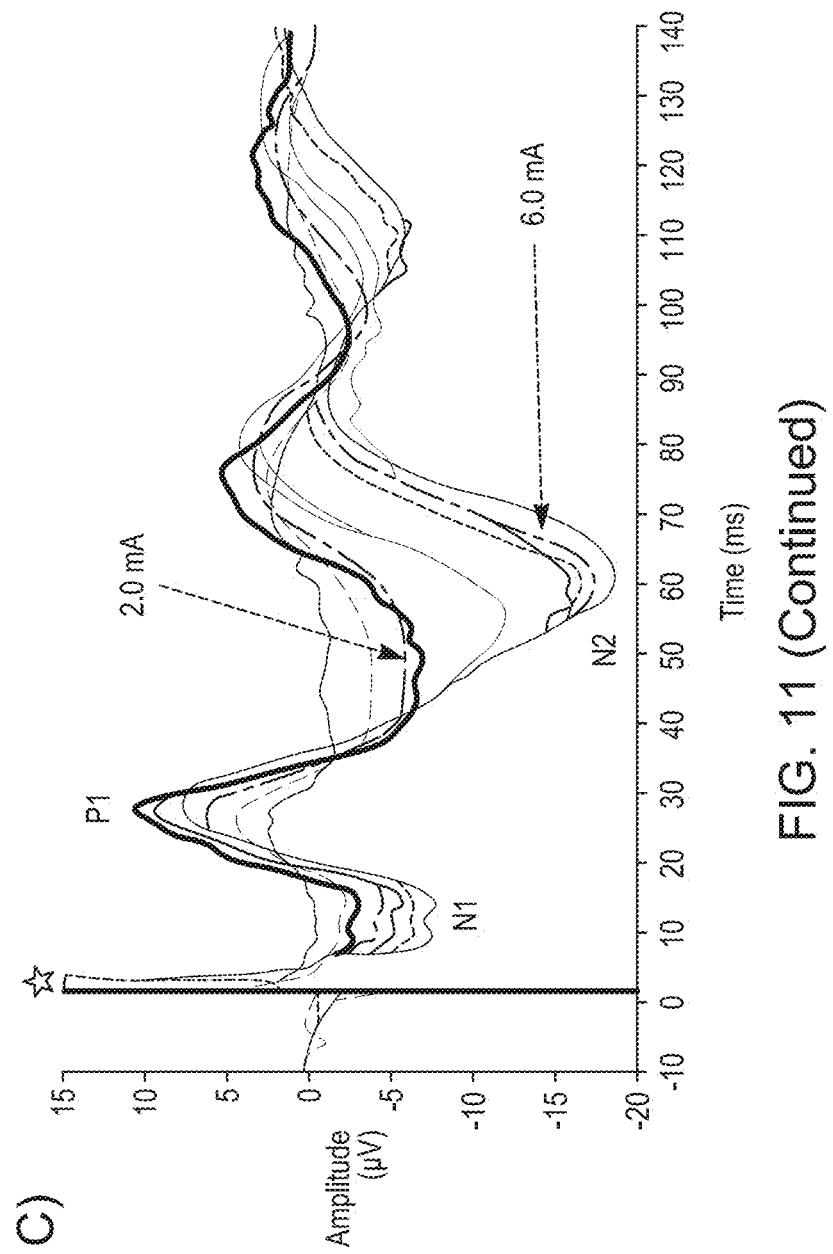
Figure 11:
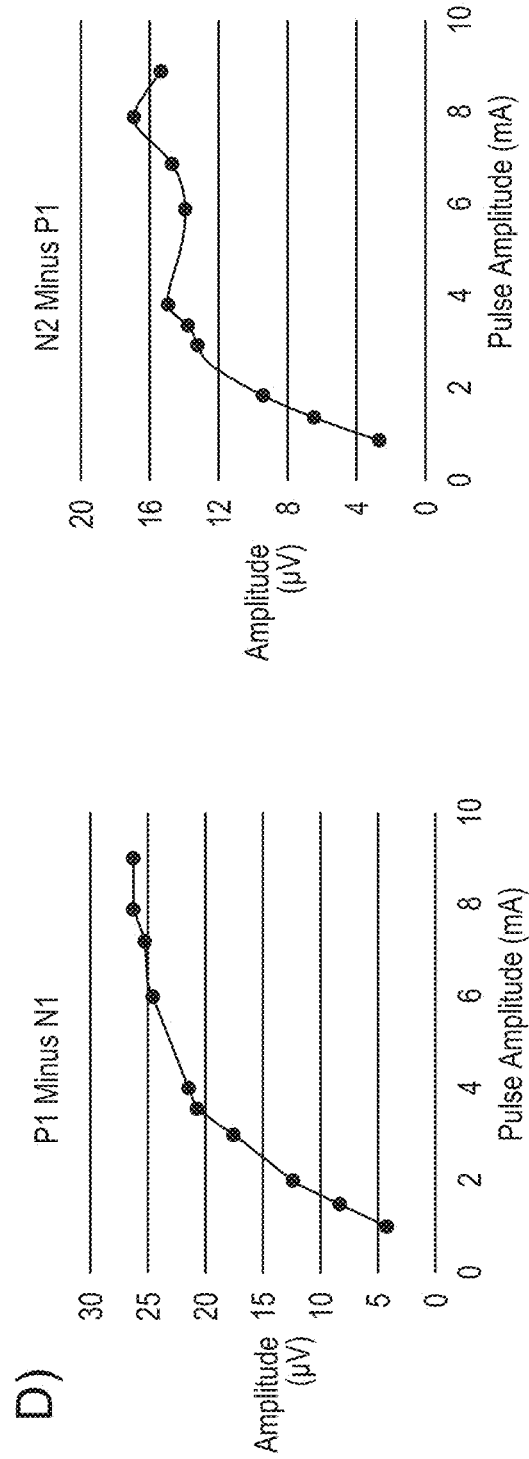

FIG. 10 shows DBS induced changes in various behavioral metrics. Top Row: shows an exemplar trace from dynamometer during a squeeze task and the corresponding measures that can be derived. Response time is the time spanned between GO cue and movement onset. Reach time is the time spanned between onset and target. Relaxation time is the time spanned between target and complete session of movement. Relaxation time was divided into slow and fast phase based on changes in velocity. Reach and relaxation rates were computed by normalizing the magnitude of movement by time. The Bottom row shows data from a testing session. The left panel shows averaged force data (multiple trials) during DBS OFF and DBS ON conditions. The middle panel shows % changes in response times when DBS was ON compared to DBS OFF. The right panel shows % change in response rates when DBS was ON compared to DBS OFF.

Step 5

It is feasible to characterize and quantify the magnitude of the change in cerebral cortical activity evoked by stimulation of the cerebellar dentate region as a means of titrating therapeutic charge (pulse amplitude×pulse width) delivery. We have discovered that responses to low-frequency electrical stimulation of the cerebellar dentate region can be time-locked average to yield reproducible spatiotemporal pattern of cerebral cortical activity as recorded using surface, or scalp, EEG electrodes (FIG. 11A). FIG. 11A shows an overview of the recording set-up, depicting a patient with an existing implanted pulse generator and DBS lead implant who has been fitted with scalp recording electrodes. Stimulus pulses are delivered by the implanted pulse generator and detected as electrical artifact in the EEG signal for use as a time-locking signal. In the upper right of FIG. 11A, an example mapping of responses recorded across multiple EEG electrode sites across the scalp is depicted.

Stimulus pulses may be delivered either by an external pulse generator in cases where the proximal end of the DBS lead is externalized or using a previously implanted pulse generator as the source. Analysis of the spatiotemporal distribution of these responses can be used to identify cortical regions that are maximally modulated in response to the stimulus pulse as a function of time post-stimulation (FIG. 11B). By varying specific features of stimulation, including pulse amplitude, pulse width, and electrode/contact through which stimulation is delivered, it is possible to characterize further the degree of cortical modulation using different quantitative metrics (e.g., RMS power, peak-to-peak amplitude, peak latency). In FIG. 11B, the upper drawing represents a butterfly plot, which overlays the averaged electroencephalographic response recorded from multiple sites across the scalp to a single set of DBS parameters. The stimulus pulse (denoted by the star) evokes a complex, multi-phase response that lasts for more than 100 ms post-stimulation (settings: 2.0 mA delivered at 90-microsecond pulse width). Current source density maps (bottom) highlight potential regions of interest for further characterizing changes in the evoked response as a function of pulse amplitude/width and further highlight the possibility of using the DBS evoked potential response to visualize how changes in DBS parameters steer the modulation of activity across different cortical regions.

FIG. 11C demonstrates how the overall size of the evoked response changes as a function of pulse amplitude for a single recording site (EEG site FC2) when the pulse width is maintained at 90 microseconds and the same electrode/contact is used so that electrode/contact and pulse width are consistent in this figure. In FIG. 11C, the averaged evoked response recorded from the FC2 recording site is plotted (amplitude (μV) v. time (ms)) for multiple conditions of pulse amplitude ranging from 1.0 mA to 9.0 mA. The response at 2.0 mA and 6.0 mA is highlighted for illustration purposes and the peaks used to calculate peak-to-peak amplitude changes as a function of changes in pulse amplitude are highlighted (N1: $1^{st}$ negative peak; P1: $1^{st}$ positive peak; N2: $2^{nd}$ negative peak).

Notably, for a given pulse width, the relationship between the response amplitude and pulse amplitude is non-linear and typically marked by an initial steep phase where the magnitude of the evoked response increases rapidly per unit increase in pulse amplitude, followed by a phase where the growth in magnitude is reduced per unit of amplitude increase (FIG. 11D). In practice, such a response may be used to identify, at a patient-specific level, the pulse parameters that maximize the induced cortical modulation without saturating the system. Data for making this determination may be derived from a single channel or a combination of data from multiple recording electrodes. In addition to optimizing the degree of neuromodulation the system would also improve therapeutic efficiency by minimizing the risk of waste charge delivery (e.g., additional charge that does substantially amplify the cortical response). In FIG. 11D, the peak-to-peak amplitude of the major components of the evoked response plotted as a function of cerebellar stimulus pulse amplitude for P1 minus N1 (left) and N2 minus P1 (right). It is noteworthy that both metrics suggest the onset of a plateau in the modulatory effects of DBS at pulse amplitudes above 4.0 mA, which may be useful in identifying the optimal, therapeutic stimulus amplitude.

From the above description, those skilled in the art will perceive improvements, changes and modifications. Such improvements, changes and modifications are within the skill of one in the art and are intended to be covered by the appended claims.

The following is claimed:

1. A method for configuring a deep brain stimulation (DBS) system for a patient, the method comprising:
   instructing the patient to perform or attempt to perform at least one motor task;
   in response to the patient performing or attempting to perform the at least one motor task, receiving, by a system comprising a processor, electrophysiology data from a plurality of DBS electrodes implanted in at least one cerebellar pathway connecting to a brainstem, a diencephalon, or a cerebrum of the patient;
   based on the electrophysiology data, identifying, by the system, at least one of the plurality of DBS electrodes implanted closest to a neuronal population involved in control of the at least one motor task as potential stimulation electrodes;
   in response to the patient performing or attempting to perform the at least one motor task, receiving, by the system, electroencephalogram (EEG) data corresponding to at least one scalp EEG from a plurality of EEG scalp electrodes;
   determining, by the system, at least one of the potential stimulation electrodes that is at an optimal electrode location for the patient to deliver the DBS by comparing the potential stimulation electrodes with the EEG data of the plurality of EEG scalp electrodes, wherein the comparing includes weighing the potential stimulation electrodes with the EEG data recorded while the patient performed or attempted to perform the at least one motor task;

selecting, by the system, the at least one of the potential stimulation electrodes that is at the optimal electrode location for the patient to deliver the DBS based on the weighing;

determining, by the system, optimal parameters for the DBS to be delivered by the at least one of the potential stimulation electrodes at the optimal electrode location for the patient, wherein the optimal parameters for the DBS are titrated to select a lowest amplitude that produces a robust response indicative of modulation with minimum side effects; and outputting, by the system, the optimal parameters for the DBS and a location of the at least one of the potential stimulation electrodes that is at the optimal electrode location for the patient to deliver the DBS to guide configuration of the DBS system for the patient to treat a neurological disorder negatively affecting the patient during the at least one motor task.

2. The method of claim 1, further comprising configuring the DBS system, by the system, so that the at least one of the potential stimulation electrodes delivers the DBS at the optimal parameters.

3. The method of claim 1, wherein the at least one motor task comprises moving an arm, a hand, a finger, a foot, or a leg.

4. The method of claim 1, wherein the electrophysiology data comprises one or more local field potentials (LFPs) measured by the plurality of DBS electrodes during the at least one motor task.

5. The method of claim 4, wherein the electrophysiology data comprises a power in a theta, alpha, beta, and/or gamma oscillatory band of each LFP signal and/or a power change in the theta, alpha, beta, and/or gamma oscillatory band of each LFP signal.

6. The method of claim 1, wherein the plurality of scalp EEG electrodes are located over the patient's primary motor cortex, secondary motor cortex, primary sensory cortex, and/or secondary sensory cortex.

7. The method of claim 1, wherein the change in the EEG data is a change in event related desynchronization (ERD) and/or event related synchronization (ERS).

8. The method of claim 7, wherein the change in the EEG is seen in theta, alpha, beta, and/or gramma band activity in the EEG data.

9. The method of claim 1, wherein the selecting at least one of the potential stimulation electrodes to deliver the DBS is further based on a change in an instrumentation-based motor behavior.

10. The method of claim 1, wherein the optimal parameters are parameters that provide a response indicative of modulation with a lowest magnitude of stimulation.

11. The method of claim 1, wherein the optimal parameters comprise at least one of an optimal stimulation amplitude, one or more optimal pulse or burst parameters, an optimal stimulation frequency, and an optimal stimulation pulse width.

12. The method of claim 1, before the instructing, excluding at least a portion of the plurality of DBS electrodes and/or stimulation parameters known to cause undesired side effects.

13. The method of claim 12, wherein the excluding is based on an initial monopolar review specific to the patient.

14. The method of claim 12, wherein the excluding is based on data specific to a population comprising at least one similar patient.

15. A system that configures a deep brain stimulation (DBS) system for a patient, the system comprising:

a memory storing instructions;

a processor to access the memory and execute the instructions to:

in response to the patient performing or attempting to perform at least one motor task, receive electrophysiology data from a plurality of DBS electrodes implanted in at least one cerebellar pathway connecting to a brainstem, a diencephalon, or a cerebrum of the patient and electroencephalogram (EEG) data corresponding to at least one scalp EEG from a plurality of EEG scalp electrodes;

based on the electrophysiology data, identify at least one of the plurality of DBS electrodes implanted closest to a neuronal population involved in control of the at least one motor task as potential stimulation electrodes;

determine at least one of the potential stimulation electrodes that is at an optimal electrode location for the patient to deliver the DBS by comparing the potential stimulation electrodes with the EEG data of the plurality of EEG scalp electrodes, wherein the comparing includes weighing the potential stimulation electrodes with the EEG data recorded while the patient performed or attempted to perform the at least one motor task;

select the at least one of the potential stimulation electrodes that is at the optimal electrode location for the patient to deliver the DBS based on the weighing;

determine optimal parameters for the DBS to be delivered by the at least one of the potential stimulation electrodes the optimal electrode location for the patient, wherein the optimal parameters for the DBS are titrated to select a lowest amplitude that produces a robust response with minimum side effects; and output the optimal parameters for the DBS and a location of the at least one of the potential stimulation electrode that is at the optimal electrode location for the patient to deliver the DBS to guide configuration of the DBS system for the patient to treat a neurological disorder negatively affecting the patient during the at least one motor task.

16. The system of claim 15, wherein the processor further executes the instructions to configure the DBS system so that the at least one of the potential stimulation electrodes delivers the DBS at the optimal parameters.

17. The system of claim 15, wherein the electrophysiology data comprises one or more local field potentials (LFPs) measured by the plurality of DBS electrodes during the at least one motor task.

18. The system of claim 15, further comprising the plurality of scalp EEG electrodes, and a task component configured to assist the patient in performing or attempting to perform the at least one motor task.

19. The system of claim 15, wherein the optimal parameters are parameters that provide a response indicative of modulation with a lowest magnitude of stimulation.

20. The system of claim 15, wherein the processor further executes the instructions to exclude at least a portion of the plurality of DBS electrodes and/or stimulation parameters that cause undesired side effects based on an input received from a medical professional, an instrument monitoring behavior of the patient, or the patient.

* * * * *